(12) United States Patent
Russell

(10) Patent No.: US 9,433,372 B2
(45) Date of Patent: Sep. 6, 2016

(54) SYSTEM METHOD AND DEVICE FOR PROVIDING AN AUTOMATED FITNESS TEST

(75) Inventor: Brian K. Russell, Crownsville, CT (US)

(73) Assignee: Zephyr Technology Corporation, Annapolis, MD (US)

( * ) Notice: Subject to any disclaimer, the term of this patent is extended or adjusted under 35 U.S.C. 154(b) by 1054 days.

(21) Appl. No.: 13/331,382

(22) Filed: Dec. 20, 2011

(65) Prior Publication Data
US 2013/0023739 A1 Jan. 24, 2013

Related U.S. Application Data

(60) Provisional application No. 61/426,827, filed on Dec. 23, 2010.

(51) Int. Cl.
A61B 5/00 (2006.01)
G06F 19/00 (2011.01)
A61B 5/08 (2006.01)
A61B 5/01 (2006.01)
A61B 5/0205 (2006.01)
A61B 5/024 (2006.01)
A61B 5/11 (2006.01)

(52) U.S. Cl.
CPC ............... *A61B 5/0816* (2013.01); *A61B 5/01* (2013.01); *A61B 5/0205* (2013.01); *A61B 5/02438* (2013.01); *A61B 5/1118* (2013.01); *A61B 5/6831* (2013.01); *G06F 19/34* (2013.01); *G06F 19/3406* (2013.01); *A61B 2503/10* (2013.01); *A61B 2562/0219* (2013.01)

(58) Field of Classification Search
CPC .... A61B 2503/10; A61B 5/02; A61B 5/083; A61B 5/4866; A61B 5/145; A61B 5/11; A61B 5/1118; A61B 5/72; A63B 24/0062; A63B 2024/0065; A63B 69/0028; G06F 19/34; G06F 19/3431
See application file for complete search history.

(56) References Cited

U.S. PATENT DOCUMENTS

| 5,810,722 | A | * | 9/1998 | Heikkila | 600/300 |
| 6,174,289 | B1 | * | 1/2001 | Binder | 600/532 |
| 6,450,967 | B1 | * | 9/2002 | Wu | 600/500 |
| 2005/0065443 | A1 | * | 3/2005 | Ternes | 600/509 |
| 2007/0249949 | A1 | * | 10/2007 | Hadley | 600/519 |
| 2011/0166463 | A1 | * | 7/2011 | Xi | 600/509 |

FOREIGN PATENT DOCUMENTS

WO WO 2009133248 A1 * 11/2009

* cited by examiner

Primary Examiner — William Thomson
Assistant Examiner — Marie Archer

(57) ABSTRACT

Provided are a system, method and device for determining one or more physiological parameters of a person.

15 Claims, 5 Drawing Sheets

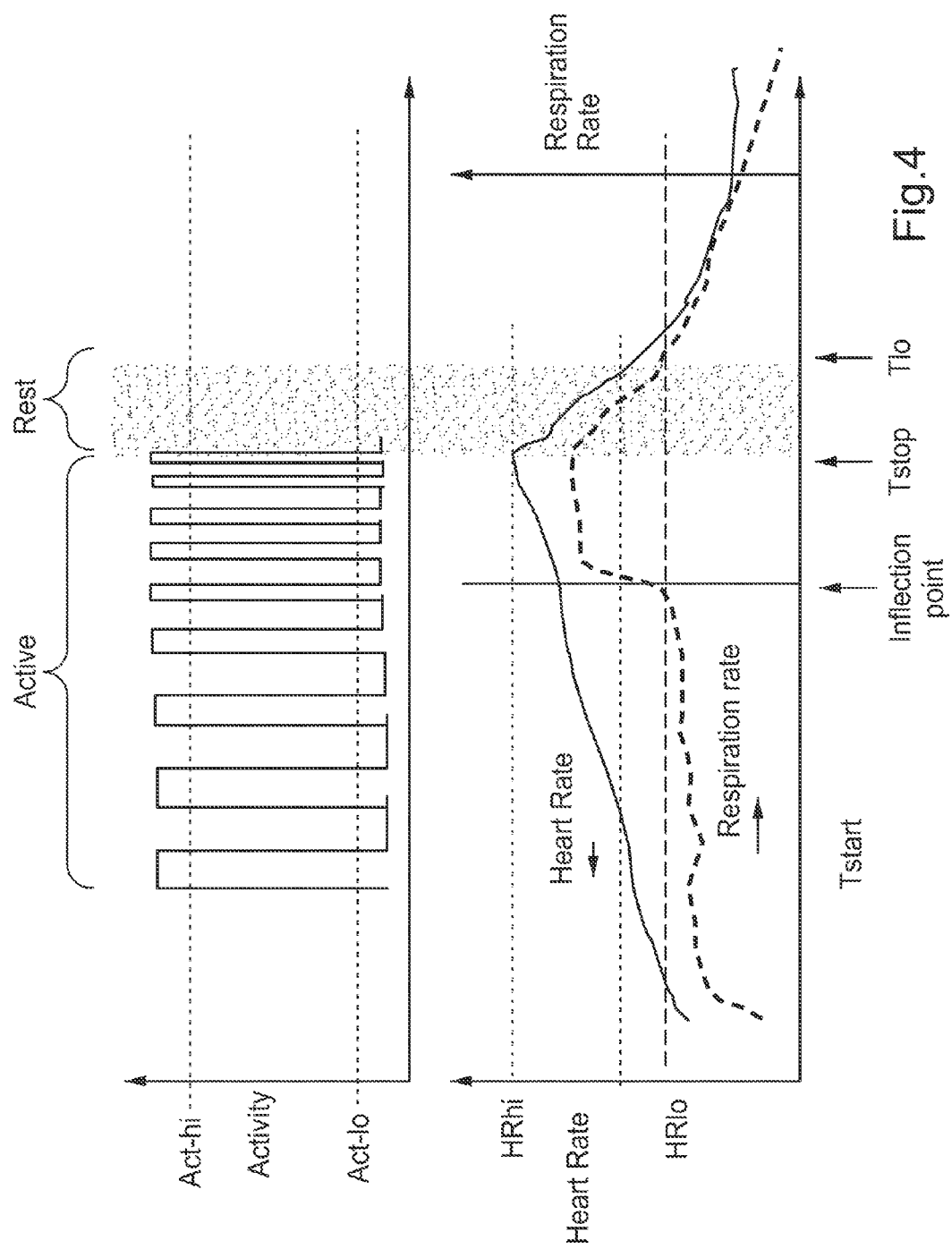

SYSTEM METHOD AND DEVICE FOR PROVIDING AN AUTOMATED FITNESS TEST

CROSS-REFERENCE TO RELATED APPLICATIONS

This application claims priority to U.S. Provisional Patent Application Serial No. 61/426,827, filed Dec. 23, 2010, the complete disclosure of which is incorporated herein by reference.

FIELD OF THE INVENTION

The present invention generally relates to physiological data processing and more particularly, to a system, method and device for determining one or more physiological parameters of a person.

BACKGROUND OF THE INVENTION

It is well known that a fitness test is an effective way to measure $VO_2$ max (also sometimes referred to as maximal oxygen consumption, maximal oxygen uptake or aerobic capacity) and is the maximum capacity of an individual's body to transport and utilize oxygen during incremental exercise, which reflects the physical fitness of the individual). Other measures of fitness include measuring an individual's anaerobic threshold (i.e., exercise intense enough to trigger anaerobic metabolism), maximum heart rate, and heart rate recovery. These parameters are typically measured using a ramped effort test or a constant velocity at a speed that can not be sustained. A problem with this test is that there are various measurements and equipment required including, for example, a gas analysis machine, a sticky patch halter monitor for EKG and heart rate, and a treadmill.

Consequently, typically such fitness tests cannot be performed in the field.

It would be desirable to be able to perform such fitness tests in the field (i.e., not in a lab or medical facility) and without at least some of the above equipment.

These and other advantages may be provided by one or more embodiments of the present invention.

BRIEF DESCRIPTION OF THE DRAWINGS

The invention is further described in the detailed description that follows, by reference to the noted drawings by way of non-limiting illustrative embodiments of the invention, in which like reference numerals represent similar parts throughout the drawings. As should be understood, however, the invention is not limited to the precise arrangements and instrumentalities shown. In the drawings:

FIG. 4 is a graphic representation of respiration, heart rate and activity, in accordance with another example embodiment of the present invention.

DETAILED DESCRIPTION OF ILLUSTRATIVE EMBODIMENTS

In the following description, for purposes of explanation and not limitation, specific details are set forth, such as particular networks, communication systems, computers, terminals, devices, components, techniques, data and network protocols, software products and systems, operating systems, development interfaces, hardware, etc. in order to provide a thorough understanding of the present invention.

However, it will be apparent to one skilled in the art that the present invention may be practiced in other embodiments that depart from these specific details. Detailed descriptions of well-known networks, communication systems, computers, terminals, devices, components, techniques, data and network protocols, software products and systems, operating systems, development interfaces, and hardware are omitted so as not to obscure the description.

The present invention provides an automated method of determining HR (heart rate), BR (breathing rate), activity (e.g., speed) and automatically triggering (e.g., based on the decrease in activity) a data analysis to determine the maximum heart rate (HRmax), the heart rate recover (HRR), the anaerobic threshold (AT), and the aerobic capacity.

A person's physiology changes based on speed of movement, level of activity and posture. The present invention addresses the issue of automatically testing various physiological states when using sensors for short term and long term monitoring (such as in the field) of bioelectric signals of a person. When a person is in the field (e.g., at home, in a gym, at work, etc.), the clinician or coach cannot make a manual assessment of the person's level of activity, heart rate, breathing rate and other parameters. The present invention provides a novel way to remotely determine these values by using a combination of biomechanical sensors, physiological sensors and algorithms that process these values over time. This specific example embodiment automatically determines one or more parameters that are a measure of the person's fitness.

The present invention uses a breathing sensor and a heart rate sensor. Some embodiments also may use an accelerometer. A single sensor device may be employed to provide raw data, which is processed by software that separately outputs the person's heart rate, breathing rate and in some embodiments speed (or other level of activity). When a sequence of activities is detected, such as an activity level of a minimum threshold followed by a rest period extending for a minimum time period, the previously measured and stored heart rates and breathing rates can be processed to determine one or more fitness parameters.

Figure 3A:
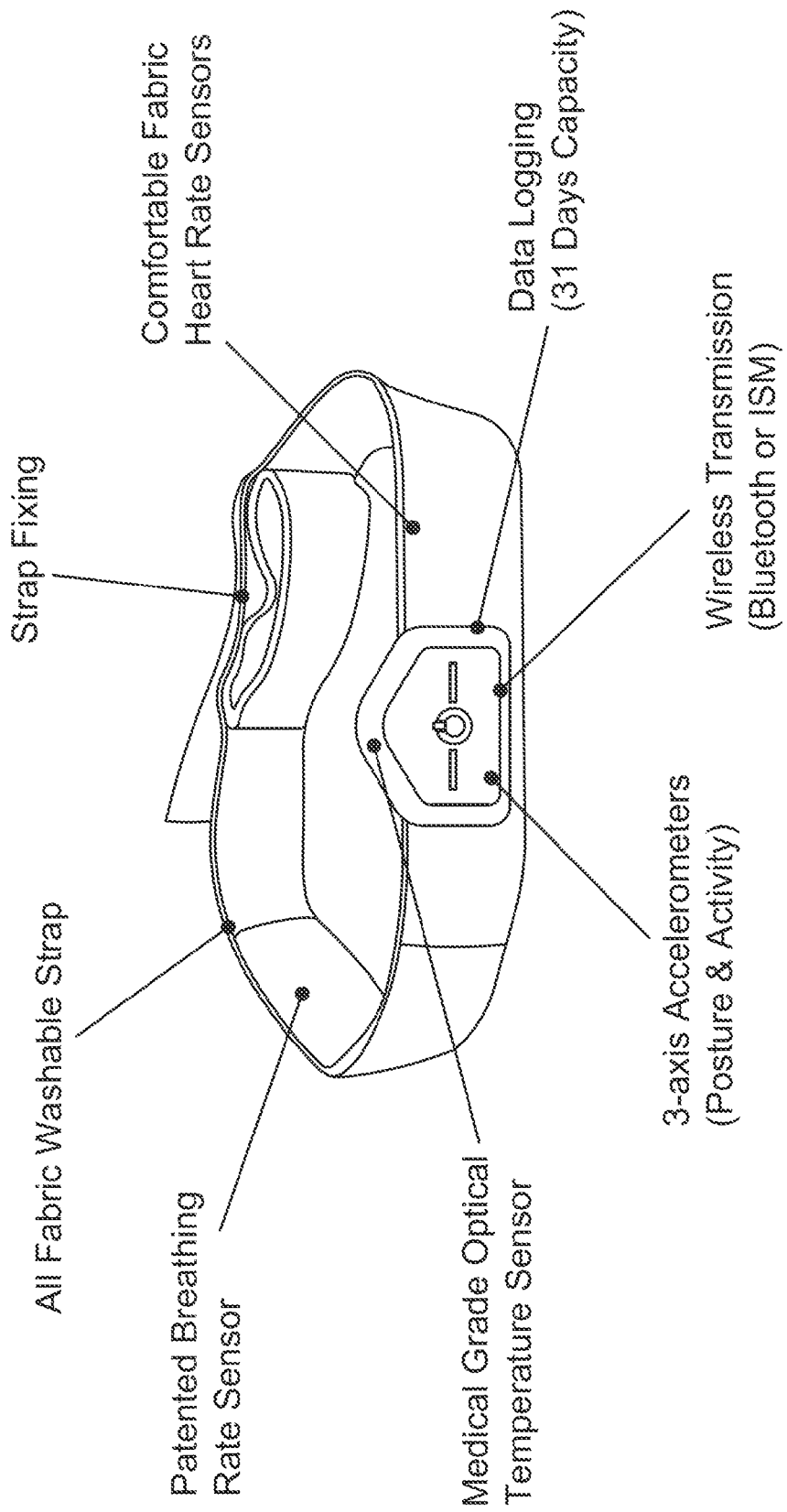
FIG. 3 depicts a BioHarness that may be used to collect (and process data), in accordance with an example embodiment of the present invention.
Figure 3B:
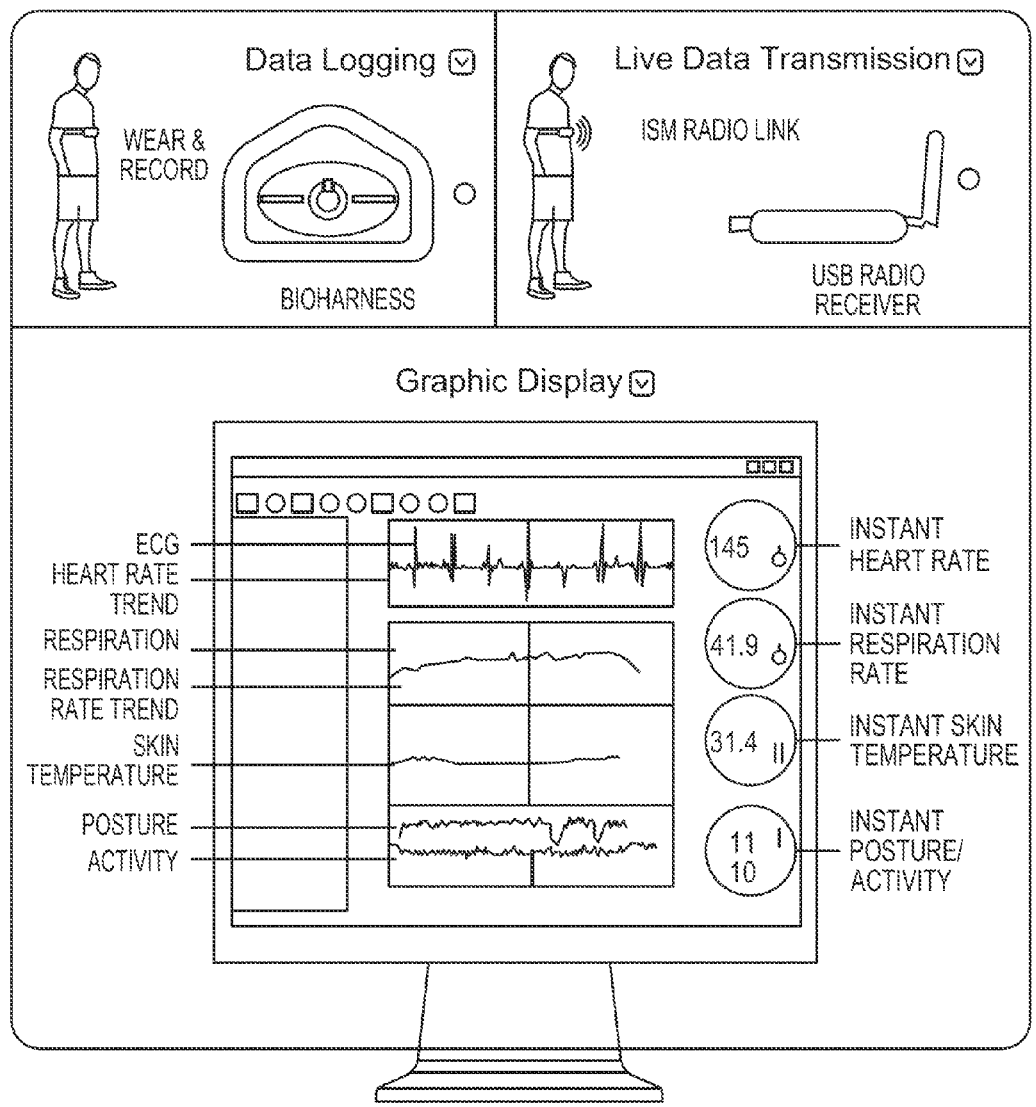

The data used by embodiments of the present invention may be collected and processed by a device such as a BioHarness, which is commercially available and manufactured by Zephyr Technology of Annapolis, Md. See FIG. 3. The device measures heart rate, breathing rate, temperature, activity (via an accelerometer), and posture, is battery powered and worn as a chest strap. It includes a Bluetooth wireless transceiver and internal memory. In other embodiments, the sensor device may be integrated and/or attached to a garment (e.g., shirt). The person may wear the device at home and/or work (or in a clinic environment). The data from the biomechanical and physiological sensors (and in some embodiments, environmental sensors) is regularly collected and stored in memory. Upon detection of certain physiological data (an acceptable activity envelope), the algorithm processes the stored data to determine one or more fitness parameters for the wearer. The algorithm may be executed on the sensor device (e.g., the BioHarness) or a computer that receives the data from the sensor device. Activity may also or alternately be measured using an accelerometer such as a tri axial MEMS (micro electronic machine sensor).

Figure 1:
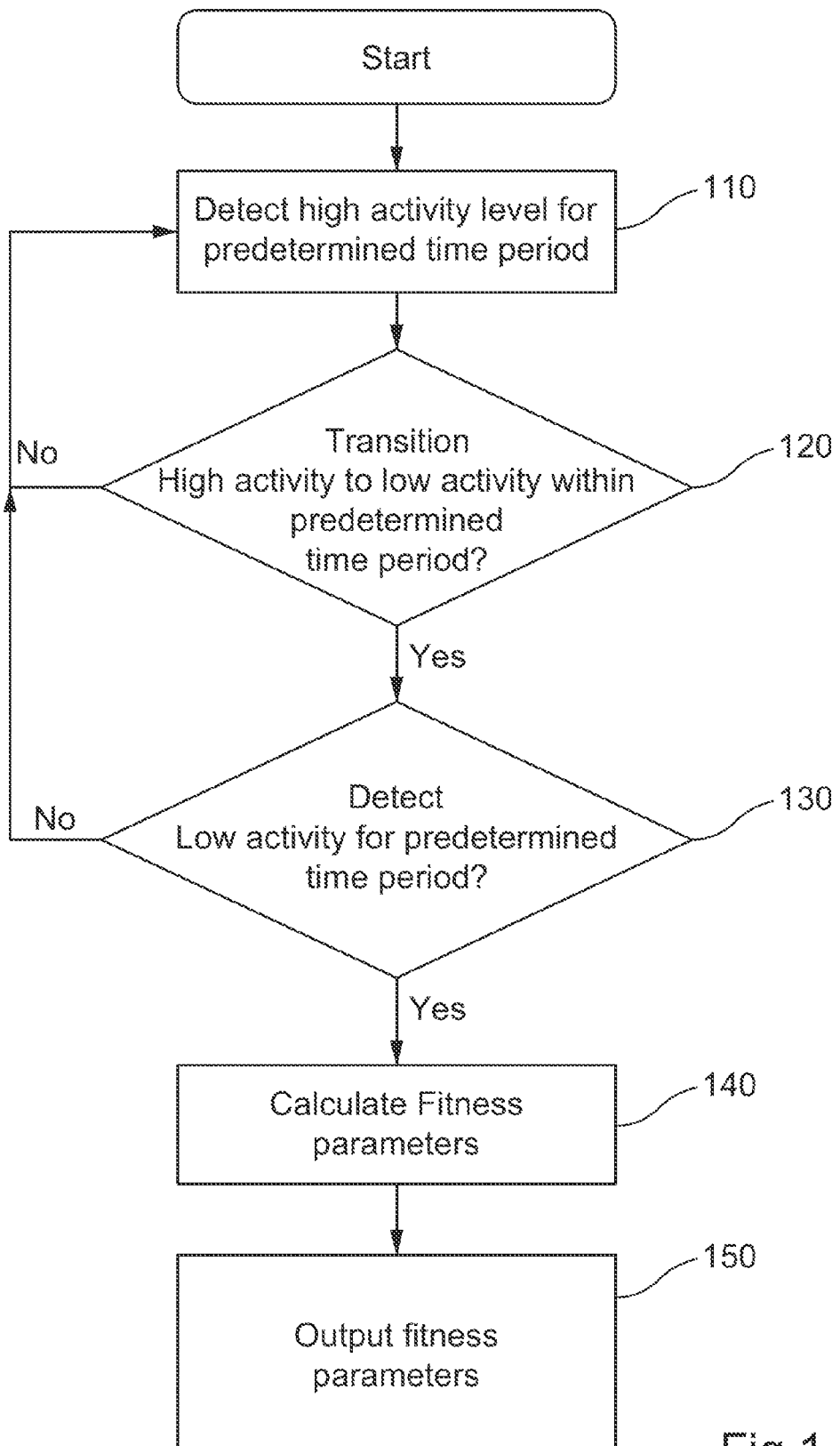
FIG. 1 is a flow chart of a process, in accordance with an example embodiment of the present invention.

One example algorithm for computing various physiological parameters is described below in conjunction with FIGS. 1 and 2. The person under test may wear the BioHarness or other sensor device(s) to continually (or regularly) monitor the person's heart rate, activity, breathing and other physiological data. Although the person's movement need not be instructed, the person must in engage in vigorous activity that is preferably increasingly challenging. For example, the person may perform a prescribed activity such as running on a treadmill wherein the required power output (e.g., incline) increases incrementally each minute. The system will process the data to determine the fitness parameters when the sequence of the person activity satisfies certain parameters. As discussed above, data of the person's activity (e.g., speed), breathing rate, and heart rate is continually monitored and stored. In embodiments wherein the person is performing a prescribed activity, the activity (e.g., speed and incline) may be retrieved from memory based on a known (or user indicated) starting time and the duration of the test. In other words, if the speed is constant and the incline increases by one degree each minute, after 9.5 minutes the incline would be known to be 9 degrees. When the person's activity level (e.g., speed) satisfies a triggering envelope, the stored heart rate data and breathing rate data is processed to determine the fitness parameters.

Figure 2:
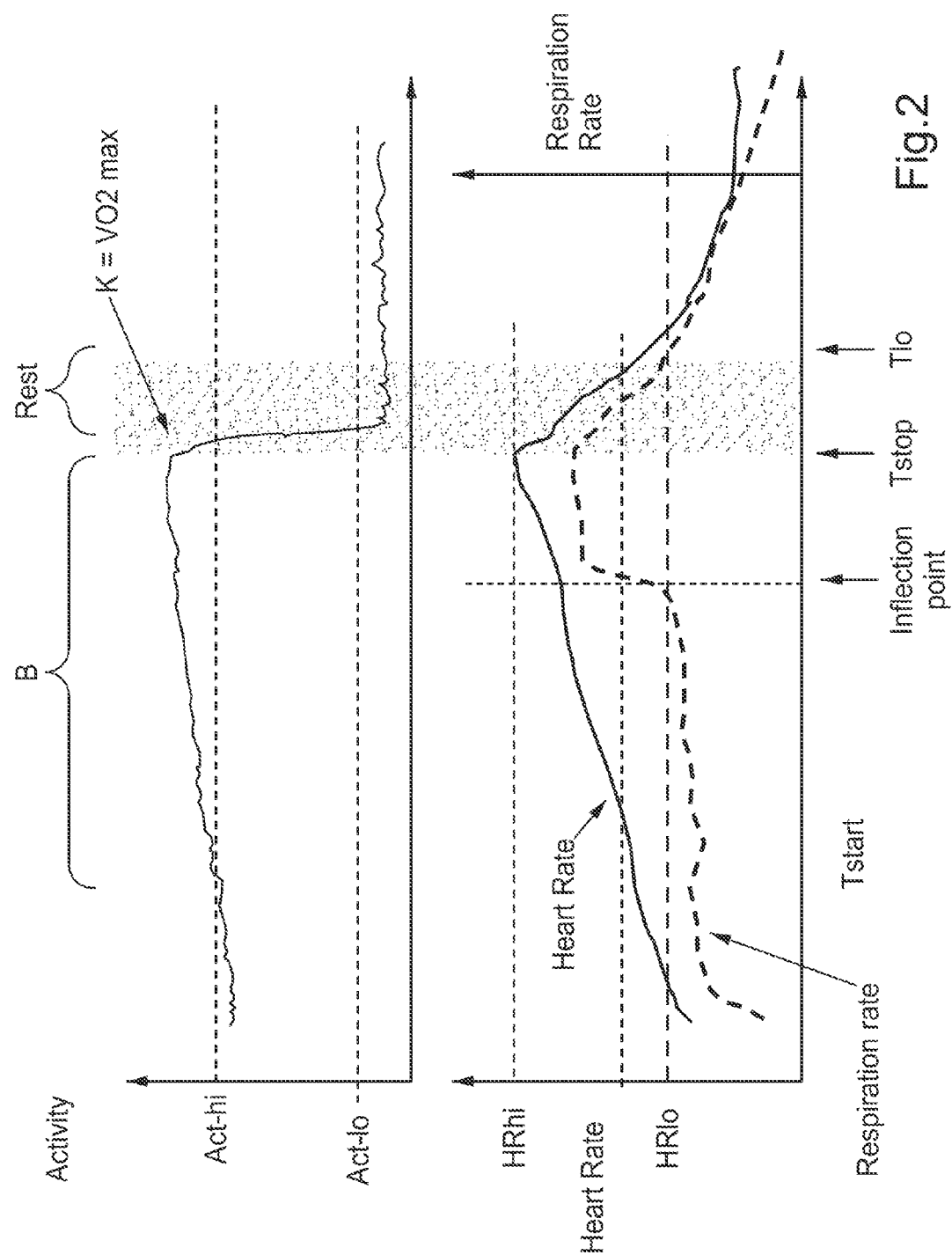
FIG. 2 is a graphic representation of respiration, heart rate and activity, in accordance with an example embodiment of the present invention.

FIG. 2 includes two graphs. The top graph depicts an activity level graph. An example of a triggering envelope includes the person's level of activity exceeding a first predetermined threshold, indicated by Act-hi on the graph, for a first predetermined time period. In this example, the person maintained an activity level greater than the threshold Act-hi for a time period indicated by the bracket B on the graph. The second portion of this example triggering envelope includes the person's level of activity falling below a second predetermined threshold, indicated by Act-lo on the graph (transitioning within a maximum time period), and remaining below the second threshold for a second predetermined time period. It is worth noting that the person's activity level transitioned from high, such as running, to very low, such as sitting, standing, or walking, in a very short time period, which may also form part of a triggering envelope.

In another embodiment, the person may be instructed to perform an activity (that is increasingly challenging) until the person can no longer maintain the activity level, and then stop (e.g., sit down or simply stand). For example, the person may be instructed to run on a treadmill at a constant speed for as long as possible while the angle of incline repeatedly increases. In such an embodiment, the trigger may occur when the user indicates that he or she can no longer continue (and the treadmill is stopped). Other embodiments may employ other triggering envelopes.

Upon satisfaction of the triggering envelope, the data stored during the envelope may be processed to determine one or more fitness parameters for the person. In the bottom graph of FIG. 2, heart rate is represented by the solid line and respiration is represented by the dashed line.

Maximum Heart Rate or HRmax may be determined by processing the heart rate data to determine the highest heart rate during the activity by performing a moving average (e.g., with a 10 or 15 second trailing window).

Heart Rate Recovery or HRR, is the decrease in heart rate from the time activity stops (Tstop) to a predetermined time (Tlo). In some embodiments of the present invention, the algorithm may compute the HRR using data of the heart rate thirty seconds after the activity stops (i.e., after the activity falls below the Act-lo threshold) and is computed as the high heart rate (just prior to stoppage of the activity) minus the heart rate thirty seconds after stopping the activity or, with reference to the bottom graph of FIG. 2:

$HRR=HRhi-Hrlo.$ $VO_2$ max or aerobic capacity may be computed by the following equation based on the data at time K (top graph) when the person stopped the activity (quit) because the person could no longer continue. The required data may be received from the treadmill or retrieved from memory based on the duration of the test as discussed above.

$VO_2 \max=(\text{speed}\times16.67\times0.2)+[(\text{speed}\times16.67\times\text{inc}/100)\times1.8\times0.5]+3.5$ wherein:
    inc=the % incline of the treadmill at end of test (at K); and
    speed=the speed of the user during the test.

Thus, this test is a maximal fitness test because the person continues as long as possible. The units of $VO_2$ max may be ml/kg/min.

Anaerobic Threshold (AT) is a useful measure for deciding exercise intensity for training and racing in endurance sports (e.g. long distance running, cycling, rowing, swimming, motocross, and cross country skiing), and can be increased greatly with training. Anaerobic threshold is sometimes referred to as lactate threshold, aerobic threshold, maximal lactate steady state, onset of blood lactate accumulation (OBLA) and anaerobic zone. Anaerobic threshold may be determined by the measured activity level at the inflection point of the respiration rate. Thus, the algorithm may process the respiration data to identify the inflection point of the respiration data and then determine (retrieve) the activity (incline at that respiration rate).

Data may automatically collected in the device that includes respiration and heart rate and also may determine activity level (based on the starting time) or measure the activity (via an accelerometer which measures movement in three axes), When an acceptable activity envelope is detected (as illustrated by processes 110, 120, and 130 of FIG. 1), at 140 the invention may compute HRmax, HRR, anaerobic threshold, and/or aerobic capacity as described above. The computed fitness parameters may be output at 150.

Referring to FIG. 2, when the activity level rises above Act-hi for a first minimum time period (B), followed by a reduction in activity (i.e., transition to a low activity) within a second time period and the reduced activity level extends (remains low) for another minimum time period (Rest), the collected data may be processed (immediately or some time thereafter). To process the data, the software identifies the inflection point of the breathing rate (i.e., respiration data) that occurred during the first minimum time period (B). The AT is then determined as a percentage of the aerobic capacity ($VO_2$ max). Specifically, the AT is computed using the equation above divided by the $VO_2$ max or more specifically:

$AT=[(\text{speed}\times16.67\times0.2)+[(\text{speed}\times16.67\times\text{inc}/100)\times1.8\times0.5]+3.5]/VO_2 \max:$ wherein:
    inc=the % incline of the treadmill at the inflection point;
    speed=the speed of the user during the test; and VO₂ max=computed from above.

While the aerobic capacity of an individual will generally remain constant (except for aging), the person's anaerobic threshold will vary based on the person's fitness level, dehydration, fatigue of the person's muscular system, fatigue of the nervous system, and other factors. In the bottom graph of FIG. 2, the further to the right on the graph that the infection point occurs (and the greater the percentage of the aerobic capacity), the more fit the person is (assuming fatigue, dehydration, etc. are constant). Thus, a person may periodically (e.g., weekly) perform the aerobic capacity and anaerobic threshold tests to determine whether their training is improving their fitness or whether they are over training (which may be indicated if the inflection point moved away from the VO₂ max toward the left).

Generally, the above described method is more accurate than using the heart rate to determine AT which generally has a much more flat curve during high exertion thereby reducing the accuracy of the computed result.

Anaerobic threshold also may be computed from a submaximal test in which the user stops the activity prior to reaching complete exertion (point K) but after the infection point. In a sub-maximal test, the person's aerobic capacity may be determined from reference tables that provide an aerobic capacity based on the person's age, gender and height.

The example of FIG. 2 is described in the context of a continuous exercise. FIG. 4 depicts an example of the present invention in which the person is not performing continuous exercise, but is performing an interval exercise. In this fitness test, the person is instructed to sprint between two cones. This automated fitness test allows many people to take part concurrently. A traditional beep test (or shuttle run) decreases the time to run between two stationary cones until the person does not manage to finish the run between the cones within the allotted time. The problem with this approach is that the person can be stationary once they reach one cone (finish a run) until the next time period begins. In the present invention, the activity detection algorithm determines when the overall test has stopped by detecting inactivity for a predetermined time period (indicated by the Rest period on the top graph of FIG. 4) and then uses the stored data to determine the duration of the last high activity. Thus, when an acceptable activity envelope is detected (by detection of a minimum rest period, which is longer than any rest time between intervals of activity) the invention may compute the HRmax, HRR, anaerobic threshold, and/or aerobic capacity via any suitable method known to those skilled in the art. Thus, the invention may be employed to determine fitness parameters for both interval and continuous activities.

Algorithms of the present invention can be used while a person is carrying out random events (or exercises) or is performing requested (known) behaviour.

The present invention may be embodied, at least in part, as a computer system (one or more co-located or distributed computers) or cluster executing one or more computer programs stored on a tangible medium. The algorithm may be executed (and computer system located) local or remote from the user. The algorithm may be executed on a computer system that also includes other functions such a telephone or other device (e.g., an IPhone®, IPad®, or Blackberry®), which may have processing and communications capabilities. As discussed, the algorithm may also be stored and executed on the collection device.

It is to be understood that the foregoing illustrative embodiments have been provided merely for the purpose of explanation and are in no way to be construed as limiting of the invention. Words used herein are words of description and illustration, rather than words of limitation. In addition, the advantages and objectives described herein may not be realized by each and every embodiment practicing the present invention. Further, although the invention has been described herein with reference to particular structure, materials and/or embodiments, the invention is not intended to be limited to the particulars disclosed herein. Rather, the invention extends to all functionally equivalent structures, methods and uses, such as are within the scope of the appended claims. Those skilled in the art, having the benefit of the teachings of this specification, may affect numerous modifications thereto and changes may be made without departing from the scope and spirit of the invention.

What is claimed is:

1. A method of determining a fitness of a person, comprising:
    monitoring a heart rate, a respiration rate and an activity level of the person with an external, body-worn sensor device;
    storing data of the heart rate, the respiration rate and the activity level of the person in a memory of the sensor device;
    determining, at the sensor device, that the activity level of the person is above a first threshold for a first predetermined time period;
    after said determining that the activity level of the person is above the first threshold for the first predetermined time period, determining, at the sensor device, that the activity level of the person is below a second threshold for a second predetermined time period;
    after said determining that the activity level of the person is below the second threshold for the second predetermined time, using the stored data to perform, at the sensor device, the processes of:
    determining a maximum heart rate for the person;
    determining a heart rate recovery for the person;
    determining an aerobic capacity for the person; and
    determining an anaerobic threshold for the person.

2. The method according to claim 1, wherein said determining a heart rate recovery for the person comprises computing a difference between the maximum heart rate for the person and a heart rate for the person occurring at a predetermined time after the activity level of the person falls below the second threshold.

3. The method according to claim 1, further comprising:
    monitoring the person while the person is running on a treadmill, the treadmill having an incline that is increased by predetermined incline intervals at predetermined time intervals and the treadmill having a known speed; and
    wherein said determining an aerobic capacity for the person comprises using the following equation:

$VO_2\ max = (speed \times 16.67 \times 0.2) + [(speed \times 16.67 \times inc/100) \times 1.8 \times 0.5] + 3.5$ wherein:
    inc=the incline of the treadmill, in percent, occurring when the activity level of the person falls below the second threshold; and
    speed=the known speed of the treadmill.

4. The method according to claim 3, wherein said determining an anaerobic threshold for the person comprises identifying the speed of the treadmill and the incline of the treadmill occurring when the respiration rate of the person reaches an identified inflection point.

5. The method according to claim 1, wherein said determining an anaerobic threshold for the person comprises identifying an inflection point in the data of the respiration rate.

6. A method of determining a fitness of a person running on a treadmill, comprising:
monitoring a heart rate, a respiration rate of the person, and an activity level of the person with an external, body-worn sensor device;
storing data of the heart rate, the respiration rate and the activity level of the person in a memory of the sensor device;
storing data of a known test in a memory including data of a time between increments in an incline of the treadmill and a speed of the treadmill;
determining, at the sensor device, that the activity level of the person is above a first threshold for a first predetermined time period;
after said determining that the activity level of the person is above the first threshold for the first predetermined time period, determining, at the sensor device, that the activity level is below a second threshold for a second predetermined time period;
after said determining that the activity level is below the second threshold, using the stored data to perform, at the sensor device, the processes of:
determining a maximum heart rate for the person;
determining a heart rate recovery for the person;
determining an aerobic capacity for the person; and
determining an anaerobic threshold for the person.

7. The method according to claim 6, wherein said determining the heart rate recovery for the person comprises computing a difference between the maximum heart rate for the person and a heart rate of the person occurring at a predetermined time after the activity level of the person falls below the second threshold.

8. The method according to claim 6, wherein said determining an aerobic capacity for the person comprises using the following equation:

$$VO_2\ max = (speed \times 16.67 \times 0.2) + [(speed \times 16.67 \times inc/100) \times 1.8 \times 0.5] + 3.5$$

wherein:
inc=the incline of the treadmill, in percent, occurring when the activity level of the person falls below the second threshold;
and
speed=the speed of the treadmill.

9. The method according to claim 8, wherein said determining an anaerobic threshold for the person comprises identifying the speed of the treadmill and the incline of the treadmill occurring when the respiration rate of the person reaches an identified inflection point.

10. The method according to claim 6, wherein said determining an anaerobic threshold for the person comprises identifying an inflection point in the data of the respiration rate.

11. A non-transitory computer readable medium comprising a computer readable program code embodied therein, said computer readable program code adapted to be executed by a processor to implement a method for generating and outputting a report that includes data of a fitness of a person running on a treadmill, the method comprising:
monitoring a heart rate, a respiration rate, and an activity level of the person with an external, body-worn sensor device;
storing data of the heart rate, the respiration rate and the activity level of the person in a memory of the sensor device;
storing data of a known test in memory including data of a time between increments in an incline of the treadmill and a speed of the treadmill;
determining, at the sensor device, that the activity level of the person is above a first threshold for a first predetermined time period;
after said determining that the activity level of the person is above the first threshold for the first predetermined time period, determining, at the sensor device, that the activity level of the person is below a second threshold for a second predetermined time period;
after said determining that the activity level of the person is below the second threshold, using the stored data to perform, at the sensor device, the processes of:
determining a maximum heart rate for the person, the maximum heart rate for the person occurring after the determining that the activity level of the person exceeds the first threshold and prior to the determining that the activity level of the person falls below the second threshold;
determining a heart rate recovery for the person;
determining an aerobic capacity for the person; and
determining an anaerobic threshold for the person.

12. The non-transitory computer readable medium according to claim 11, wherein said determining the heart rate recovery for the person comprises computing a difference between the maximum heart rate for the person and a heart rate of the person occurring at a predetermined time after the activity level of the person falls below the second threshold.

13. The non-transitory computer readable medium according to claim 11, wherein said determining an aerobic capacity for the person comprises identifying the speed of the treadmill and the incline of the treadmill occurring when the activity level of the person falls below the second threshold.

14. The non-transitory computer readable medium according to claim 13, wherein said determining an anaerobic threshold for the person comprises identifying the speed of the treadmill and the incline of the treadmill occurring when the respiration rate of the person reaches an identified inflection point.

15. The non-transitory computer readable medium according to claim 11, wherein said determining an anaerobic threshold for the person comprises identifying an inflection point in the data of the respiration rate.

* * * * *